US012589084B2

(12) United States Patent
Olson

(10) Patent No.: US 12,589,084 B2
(45) Date of Patent: Mar. 31, 2026

(54) CHOLINE BOLUS COMPOSITIONS FOR RUMINANTS

(71) Applicant: ALBERTA VETERINARY LABORATORIES LTD., Calgary (CA)

(72) Inventor: Merle Olson, Calgary (CA)

(73) Assignee: ALBERTA VETERINARY LABORATORIES LTD. (CA)

( * ) Notice: Subject to any disclaimer, the term of this patent is extended or adjusted under 35 U.S.C. 154(b) by 499 days.

(21) Appl. No.: 17/784,586

(22) PCT Filed: Dec. 11, 2020

(86) PCT No.: PCT/CA2020/051709
§ 371 (c)(1),
(2) Date: Jun. 10, 2022

(87) PCT Pub. No.: WO2021/113983
PCT Pub. Date: Jun. 17, 2021

(65) Prior Publication Data
US 2023/0000800 A1 Jan. 5, 2023

Related U.S. Application Data

(60) Provisional application No. 62/947,335, filed on Dec. 12, 2019.

(51) Int. Cl.
| | |
|---|---|
| *A61K 31/14* | (2006.01) |
| *A23K 50/10* | (2016.01) |
| *A61K 9/00* | (2006.01) |
| *A61K 9/20* | (2006.01) |
| *A61K 9/28* | (2006.01) |
| *A61K 31/07* | (2006.01) |
| *A61K 31/355* | (2006.01) |
| *A61K 31/593* | (2006.01) |
| *A61P 3/02* | (2006.01) |

(52) U.S. Cl.
CPC ............ *A61K 31/14* (2013.01); *A61K 9/0053* (2013.01); *A61K 9/2009* (2013.01); *A61K 9/205* (2013.01); *A61K 9/282* (2013.01); *A61K 31/07* (2013.01); *A61K 31/355* (2013.01); *A61K 31/593* (2013.01); *A61P 3/02* (2018.01)

(58) Field of Classification Search
None
See application file for complete search history.

(56) References Cited

U.S. PATENT DOCUMENTS

| | | | | |
|---|---|---|---|---|
| 3,056,724 | A * | 10/1962 | Marston ................. | A23K 40/35 |
| | | | | 424/490 |
| 4,867,977 | A | 9/1989 | Gailly et al. | |
| 5,093,128 | A | 3/1992 | Draguesku et al. | |
| 5,395,622 | A * | 3/1995 | Nielsen .................. | A61K 33/14 |
| | | | | 424/455 |
| 5,807,594 | A * | 9/1998 | King ...................... | A23K 40/35 |
| | | | | 424/490 |
| 6,355,281 | B1 | 3/2002 | Cerchiari et al. | |
| 7,510,584 | B2 * | 3/2009 | Cap .......................... | C11C 5/002 |
| | | | | 44/275 |
| 2007/0098810 | A1 * | 5/2007 | Lee .......................... | A61K 33/06 |
| | | | | 424/688 |

FOREIGN PATENT DOCUMENTS

| | | | | |
|---|---|---|---|---|
| WO | | 9608168 A1 | 3/1996 | |
| WO | | WO-2019204290 A1 * | 10/2019 | ........... B23K 26/362 |

OTHER PUBLICATIONS

International Search Report and Written Opinion mailed Feb. 17, 2021.
Jayprakash, et al., ""Rumen-protected choline: a significant effect on dairy cattle nutrition"", Veterinary world, Aug. 2016 (Aug. 2016), vol. 0, pp. 837-841).
Pineda, et al., ""Effect of a rumen-protected choline with calcium salts of long chain fatty acids on late lactation Holstein cows" milk yield and milk composition of middle and", Livestock Science; 2015, v. 175, pp. 47-58.

* cited by examiner

*Primary Examiner* — Bethany P Barham
*Assistant Examiner* — Peter Anthopolos
(74) *Attorney, Agent, or Firm* — Billion & Armitage

(57) ABSTRACT

Disclosed are bolus compositions for use in the treatment or prevention of hypocalcemia and choline deficiency in ruminants. The bolus compositions may comprise rumen-protected choline, one or more calcium salts, and water.

16 Claims, No Drawings

CHOLINE BOLUS COMPOSITIONS FOR RUMINANTS

This application is a National Stage Application of PCT/CA2020/051709, filed 11 Dec. 2020, which claims benefit of Application No. 62/947,335, filed 12 Dec. 2019 in the US and which applications are incorporated herein by reference. A claim of priority to all, to the extent appropriate, is made.

TECHNICAL FIELD

This disclosure generally relates to bolus compositions comprising mineral nutrients for ruminants. More specifically, this disclosure pertains to bolus compositions for rapid delivery of selected nutrients to ruminants in physiological distress due to nutrient deficiencies.

BACKGROUND

The process of calving is both physically and physiologically taxing on ruminants (e.g. bovines). In terms of physiological stresses, pregnancy, calving, and the onset of lactation can result in variety of nutritional deficiencies. These deficiencies may then in turn, physiologically debilitate affect the mother. As well, if such deficiencies are not prophylactically managed, or alternatively, appropriately treated as necessary during the course of the pregnancy, they may also affect the well-being of the calf.

For example, common nutritional deficiencies arising during pregnancy and calving include mineral and vitamin deficiencies in calcium, phosphorous, selenium, potassium, choline, sodium, and chloride as well as the vitamins A, D, and E. These deficiencies may lead to a variety of physiological and physical issues in the mother or calf, such as milk fever, muscle weakness, recumbency, and the like.

Of these deficiencies, hypocalcemia (i.e. low calcium levels in blood or tissue) may be particularly problematic. Hypocalcemia may occur following parturition, at the onset of lactation, when the calcium requirements of the ruminant may be significantly increased. In such cases, the ruminants may not be able to mobilize calcium from their bones at a fast enough rate to meet the calcium requirements for milk production. Hypocalcemia may lead to, for example, decreased milk production and immunosuppression. If left untreated, the hypocalcemia may also lead to sternal recumbency or lateral recumbency. In some cases, hypocalcemia may cause the animal become comatose or may be fatal.

Hypocalcemia is commonly treated by providing intravenous calcium borogluconate or by drenching the afflicted ruminants with a calcium salt-containing solution. Drenching involves passing a tube down the throat of a ruminant and pumping the salt-containing solution thereinto the rumen. This operation is difficult, as the animal must be restrained while simultaneously taking care not to pump the salt solution into the lungs of the animal, which may be fatal.

Another particularly problematic deficiency that may result at the time of calving in ruminants is a choline deficiency. Choline ($[CH_3]_3N^+CH_2CH_2OH$) has a variety of functions in ruminants but is most commonly associated with lipid metabolism. Choline is typically considered a "quasivitamin" in that, unlike classic vitamins, it can be synthesized endogenously. However, choline deficiencies in ruminants may still occur and further, may be difficult to detect in otherwise healthy animals due to the nature of its interaction with methionine, folic acid, and vitamin $B_{12}$. A choline deficiency in ruminants may lead to the accumulation of fat in the liver that in turn may lead to fatty liver syndrome and/or ketosis.

As will be appreciated by a person of ordinary skill in in the art, choline, upon ingestion by a ruminant, will be degraded in the rumen by the bacteria contained therein. Thus, in order to be absorbed by the ruminant, supplemental choline is typically delivered in the form of lipid-encapsulated, rumen-protected choline. The lipid encapsulation allows the choline to pass through the rumen without degrading and on to the abomasum and small intestine of the ruminant wherefrom it may then be absorbed.

Further, supplementary choline commonly is delivered to ruminants by way of addition to feeds or by drenching. The drenching process is carried out in the same manner as previously described herein and has the same associated risks. Furthermore, the ruminants may not eat a sufficient amount of choline-supplemented feed to meet their choline requirements and as a result, may still become choline deficient.

SUMMARY

Embodiments of the present disclosure generally relate to bolus compositions for use in the prevention or treatment of nutrient deficiencies in ruminants. More specifically, the bolus compositions are for use to prevent or treat hypocalcemia and choline deficiency. The bolus compositions comprise a mixture of rumen-protected choline, one or more calcium salts, and water, and are configured to rapidly dissolve in the rumen of a ruminant thereby rapidly providing supplemental choline and calcium to the animal. The bolus compositions may be administered either prior to anticipated nutritional deficiencies (e.g. to a pregnant cow just prior to calving) in order to prevent such deficiencies, or alternatively may be administered to treat a nutritionally deficient ruminant.

Thus, in one aspect of the present disclosure, there is provided a bolus composition for the prevention or treatment of hypocalcemia and/or a choline deficiency in a ruminant. The bolus may comprise about 5 wt % to about 20 wt % of a rumen-protected choline, about 65 wt % to about 85 wt % of one or more calcium salts, and about 15 wt % to about 25 wt % water.

In another aspect of the present disclosure, there is provided a use of the bolus compositions described herein for the prevention or treatment of hypocalcemia and/or a choline deficiency in a ruminant.

In yet another aspect of the present disclosure, there is provided a method of preventing or treating hypocalcemia and/or a choline deficiency in a ruminant, the method comprising administering at least one of the bolus compositions described herein to the ruminant.

DETAILED DESCRIPTION

The embodiments of the present disclosure generally relate to bolus compositions for use in the prevention or treatment of nutrient deficiencies in ruminants. The bolus compositions may be easily delivered into the digestive tract of deficient ruminants in order to rapidly supply nutrients thereto.

The bolus compositions of the present disclosure may provide a number of advantages. For example, and as will be discussed in greater detail below, the bolus compositions of the present disclosure comprise one or more calcium salts and a rumen-protected choline in such an amount that the bolus compositions are capable of simultaneously preventing or treating both hypocalcemia and choline deficiencies in ruminants.

Further, the bolus compositions of the present disclosure are solid, which means that the one or more calcium salts and the rumen-protected choline may be administered to the ruminants in a manner other than drenching. As will be appreciated, this avoids the risk of a salt solution entering the lungs of the ruminants, which may be uncomfortable and, in some cases, fatal. As well, as described above, a conventional method of administering supplemental choline to ruminants involves supplementing their feed. However, if the animals are suffering from conditions such as anorexia, they may not ingest the supplemental choline. The bolus compositions avoid such situations, as they may be administered by a rancher, producer, or veterinarian, and thus do not rely on the animal to self-administer by eating.

Furthermore, the bolus compositions may be easily manufactured as they may require minimal amounts of components to produce. As a result, manufacturing of the bolus compositions may be readily up-scaled to industrially relevant levels.

As used herein, the term "ruminant" is intended to encompass any animal that obtains nutrients by fermenting plant-based foods in a rumen prior to digestion. For example, such animals include bovines, goats, sheep, and deer. Further, as used herein, the term "bovine" is intended to encompass cattle (e.g. beef or dairy cows), bison, and buffalo.

As indicated above, ruminants have a unique digestive tract in which food is fermented prior to digestion. Specifically, and as used herein, the "ruminant digestive tract" includes an esophagus, a stomach having a rumen, a reticulum, an omasum, and an abomasum, which then connects to a small intestine and then further to a large intestine. As will be understood by a person of ordinary skill in the art, the rumen acts as the primary site of microbial fermentation in the ruminant digestive tract.

As used herein, the term "bolus" refers to a solid composition for delivery to the rumen of a ruminant. The bolus composition may have a shape that facilities easy swallowing by a ruminant. For example, the bolus composition may be generally spherical, cylindrical, capsular, torpedo-shaped, or donut-shaped. As well, the bolus composition may have at least one rounded end. The rounded end may reduce irritation of the esophagus of the ruminant by removing or softening a leading edge of the bolus composition. Advantageously, the bolus composition may be administered to the rumen of a ruminant with relative ease. For example, the bolus composition may be administered using a balling gun. As will be appreciated by a person of ordinary skill in the art, such administration is considerably easier than, for example, drenching, as the animal does not need to be as heavily restrained, and there is no risk of salt solution entering the lungs of the animal.

More specifically, an aspect of the present invention relates to bolus compositions for use to treat or prevent hypocalcemia and choline deficiency in ruminants. The bolus compositions may comprise rumen-protected choline, one or more calcium salts, and water. The bolus compositions of the present disclosure advantageously allow for the simultaneous treatment of hypocalcemia and choline deficiencies. A bolus composition according to the present disclosure, once delivered to the ruminant digestive tract, rapidly dissolves in the rumen to release and provide calcium and rumen-protected choline. The calcium is absorbed in the rumen, while the rumen-protected choline passes through to the abomasum and the small intestine, where it is then absorbed.

According to an embodiment, the bolus compositions of the present disclosure may aspect, the bolus compositions comprise two or three or more calcium salts. According to another aspect, the calcium salts may be selected from chloride, sulphate, carbonate, propionate, formate, citrate, iodate, periodate, lactate, acetate, and other salts suitable for administration to a ruminant digestive tract. According to some aspects, the bolus compositions may comprise two or three or more calcium salts having different release profiles. In such aspects, the bolus compositions may comprise, for example, one calcium salt that rapidly provides calcium to the ruminant and one calcium salt that provides a sustained release of calcium to the ruminant. According to a further aspect, the one or more calcium salts are calcium salt hydrates. According to another aspect, the one or more calcium salts may comprise calcium sulphate hemihydrate and calcium chloride dihydrate. According to a particular aspect, the calcium sulphate hemihydrate may be present in an amount of about 20 wt % to about 30 wt % and the calcium chloride dihydrate may be present in an amount of about 45 wt % to about 55 wt. %.

According to an embodiment, the bolus compositions of the present disclosure comprise rumen-protected choline in an amount of about 5 wt % to about 20 wt %. Rumen-protected choline is known to those of ordinary skill in the art such that they could select a type suitable for use in the bolus compositions present disclosure. In an aspect, the rumen-protected choline has a choline content of greater than about 60%. In a particular aspect, the rumen-protected choline has a choline content of about 80%.

According to another embodiment, the bolus compositions of the present disclosure comprise about 15 wt % to about 25 wt % water. In further embodiments, the bolus compositions also comprise additional vitamins and/or minerals to facilitate and maintain physiological and physical health of ruminants. Example vitamins and/or minerals include without limitation potassium, selenium, sodium, zinc, iodine, and phosphorus as well as vitamins A, D, and E. In additional embodiments, the bolus compositions of the present disclosure may comprise a binder. In an aspect, the binder is present in an amount of less than about 1 wt %. In a particular aspect, the binder is xanthum gum.

According to some embodiments, the bolus compositions have a weight of about 50 g to about 250 g. In such an embodiment, the bolus compositions may have a diameter of about 1 cm to about 3.5 cm and a length of about 3 cm to about 20 cm. As will be appreciated, the size of the bolus compositions may be adjusted based on the ruminant to which the bolus composition is to be administered. For example, a bolus composition prepared for administration to an adult bovine may be larger than a bolus composition prepared for administration to calves, sheep, or goats. According to an aspect, a bolus composition for administration to an adult bovine may have a weight of about 200 g to about 250 g, whereas a bolus composition for administration to calves, sheep, or goats may have a weight of about 50 g to about 100 g. Advantageously, due to the composition of the bolus compositions of the present disclosure and, if present, the use of a compatible coating, the bolus compositions are capable of dissolving in a rumen in less than about 30 minutes, even at larger sizes and weights (e.g. 250 g). The bolus compositions are therefore capable of rapidly delivering calcium and choline to ruminants. Notably, the content of calcium and choline delivered to the ruminants may be sufficient to elevate and maintain calcium levels for about for about 12 h to about 24 h and choline levels for about 7 days to about 14 days. However, it may also be desirable to administer bolus compositions 2 times to 4 times per day over the course of 1 day to 3 days for larger ruminants (e.g. adult bovines), or 1 time to 4 times per day over the course of 1 day to 3 days for smaller ruminants (e.g. calves, sheep, goats), based on the preventative measures or treatment required.

According to a further embodiment, the bolus compositions of the present disclosure may comprise a coating that is compatible with a ruminant digestive tract. That is, the coating may be any substance that allows for rapid dissolution in the rumen while also being non-irritating to the esophagus of the ruminant, which may be useful if repeat administrations of bolus compositions are required. According to one aspect, the coating may be a lipid-based coating. According to a further aspect, the coating may comprise acetyl esters of triglycerides. The coating may be included in any amount that sufficiently coats the bolus composition. According to an aspect, the coating is present in an amount of about 5g to about 10g.

According to another embodiment, the bolus compositions of the present disclosure may comprise a wick. The wick may be used during the manufacturing process to facilitate the bulk handling and transfer of the bolus compositions. In an aspect, the wick may be a biodegradable wick. As used herein, "biodegradable wick" refers to a wick that will degrade, dissolve, or decompose in the digestive tract of a ruminant. According to another aspect, the biodegradable wick may be formed of cellulose or a cellulosic material. According to a further aspect, the wick may be a removable wick. In such an aspect, the wick may be used during the production of the bolus compositions, but may be removed prior to administration to the ruminant. In aspects where the wick is removable, it may be made of a material that does not degrade, dissolve, or decompose in the digestive tract of a ruminant.

EXAMPLES

Example 1: Preparation of a Bolus Composition Comprising Calcium Sulphate Hemihydrate, Calcium Chloride Dihydrate, and Rumen-Protected Choline 4.4 kg of water and 0.2 g of xanthum gum were placed in a mixing vessel. The water and xanthum gum were mixed until the xanthum gum was dissolved and a viscous solution was produced.

11 kg of calcium chloride were then added with stirring to the viscous solution until a homogenous mixture was produced. 4.4 kg of calcium sulphate hemihydrate were then added and the mixture was stirred until homogenous once again. 1.9 kg of rumen-protected choline was subsequently added with stirring to produce a salt and choline solution.

Then, the homogenous salt and choline solution was poured into a plurality of aluminum molds, each having a cylindrical shape with a rounded bottom. Each aluminum mold had a diameter of about 1.26 in (3.24 cm) and a length of about 6 in (15.2 cm). Immediately after addition of the salt and choline solution to the molds, a cellulose wick of about 2 in (5.08 cm) in length was inserted into each salt and choline solution to a depth of about 1 in (2.54 cm). The salt and choline solutions were then allowed to set in the molds for about 24 h, during which time the solutions solidified to form the present bolus compositions, each having a weight of about 209 g.

The solidified bolus compositions were then removed from the aluminum molds and then dipped into a molten solution of acetyl esters of triglycerides at about 50° C. The dipping of the uncoated bolus compositions was done by gripping the wicks extending therefrom and submerging each uncoated bolus composition entirely into the molten solution. The bolus compositions, again using the wick, were then removed from the molten solution and the coatings were allowed to dry. Each dried coated bolus composition had a weight of about 210 g.

It is noted that the bolus compositions may also be made without using a wick. For example, the application of the coating may be completed by dipping half of an uncoated bolus composition into the molten solution and allowing the coating to dry, and subsequently dipping the remaining uncoated half of the bolus composition into the molten solution and again allowing the coating to dry.

Example 2: Bolus Composition Dissolution Test

One of the bolus compositions produced in Example 1 was assessed in a dissolution study during which, the bolus composition was submerged in 1 L of tap water having a pH of about 6.5 and a temperature of about 40° C. in a 1.5 L beaker. The conditions of the water were selected to mimic the pH and temperature of a rumen.

The bolus composition then was allowed to dissolve without stirring. The entire bolus composition dissolved in less than 30 minutes, thereby confirming the ability of the bolus composition to rapidly deliver calcium and choline to the rumen of a ruminant.

Example 3: Treatment of Ketosis in Post-Partum Dairy Cattle Using Bolus Compositions of the Present Disclosure Bolus compositions manufactured in the manner described in Example 1 were used to evaluate their effects in calving dairy cows having a parity of 3 or greater.

The experiment was conducted using 40 cattle. A first group of 20 cattle was administered two bolus compositions of present disclosure 0 to 12 hours post-calving. A second group of 20 cattle was administered a two calcium bolus compositions having no rumen-protected choline 0 to 12 hours post-calving.

Blood samples were collected from the coccygeal veins of the cattle before administration of the bolus compositions, at the time of administration (day 0), three days after administration, and 6 days after administration. Blood samples were collected at the time of morning milking on days 3 and 6. The blood samples were analyzed for their beta-hydroxybutyrate (BHB) content using a PRECISION XTRA® portable strip test system (PRECISION XTRA is a registered trademark of Abbott Laboratories Corp., Chicago, IL, USA). As will be appreciated by those of ordinary skill in the art, when an animal enters ketosis, the liver metabolizes fatty acids to provide an energy source for the animal. When the fatty acids are metabolized, ketones including acetone, acetoacetate, and BHB. BHB is generally the most stable of the ketones produced by fatty acid metabolism and thus is often used as an indicator for ketosis. In that regard, a blood BHB content of greater than 1.4 mmol/L indicates that a cow may have subclinical ketosis, while a blood BHB content of greater than 3 mmol/L indicates that a cow may have clinical ketosis.

The results from the first and second groups of cattle are shown below in Tables 1 and 2, respectively.

The results in Tables 1 and 2 were statistically analyzed to illustrate the difference in results between the first group of cattle treated with the bolus compositions of the present disclosure and the second group of cattle treated with bolus compositions having no rumen-protected choline. The results of the statistical analysis are included in Table 3.

TABLE 1

Blood BHB content of the cattle treated with bolus compositions of the present disclosure

| Cattle | | BHB Content (µmol/L) | | |
|---|---|---|---|---|
| No. | Parity | Day 0 | Day 3 | Day 6 |
| 1 | 3 | 1.09 | 1.11 | 1.21 |
| 2 | 3 | 1.01 | 1.02 | 1.02 |
| 3 | 4 | 1.31 | 1.22 | 1.12 |
| 4 | 3 | 0.86 | 0.87 | 1.01 |
| 5 | 4 | 1.41 | 1.44 | 1.47 |
| 6 | 4 | 1.21 | 1.11 | 1.10 |
| 7 | 5 | 1.31 | 1.21 | 1.20 |
| 8 | 4 | 1.16 | 1.15 | 1.03 |
| 9 | 3 | 1.44 | 1.48 | 1.49 |
| 10 | 3 | 1.01 | 1.14 | 1.22 |
| 11 | 3 | 1.23 | 1.33 | 1.33 |
| 12 | 5 | 1.57 | 1.58 | 1.04 |
| 13 | 5 | 1.44 | 1.41 | 1.01 |
| 14 | 4 | 0.65 | 0.88 | 0.98 |
| 15 | 5 | 2.11 | 1.36 | 1.66 |
| 16 | 5 | 1.89 | 1.89 | 2.01 |
| 17 | 3 | 1.31 | 1.41 | 0.99 |
| 18 | 3 | 0.93 | 0.99 | 1.12 |
| 19 | 3 | 0.99 | 0.99 | 1.11 |
| 20 | 4 | 1.87 | 1.64 | 1.80 |

TABLE 2

Blood BHB content of the cattle treated with bolus compositions having no rumen-protected choline

| Cattle | | BHB Content (µmol/L) | | |
|---|---|---|---|---|
| No. | Parity | Day 0 | Day 3 | Day 6 |
| 21 | 4 | 1.13 | 1.39 | 1.49 |
| 22 | 4 | 1.03 | 1.22 | 1.19 |
| 23 | 4 | 1.21 | 1.39 | 1.67 |
| 24 | 3 | 0.99 | 1.01 | 1.09 |
| 25 | 3 | 1.11 | 1.29 | 2.00 |
| 26 | 5 | 1.61 | 2.43 | 3.66 |
| 27 | 5 | 1.41 | 1.88 | 2.01 |
| 28 | 5 | 1.11 | 2.44 | 2.98 |
| 29 | 3 | 1.04 | 1.71 | 2.00 |
| 30 | 3 | 1.03 | 1.97 | 3.12 |
| 31 | 5 | 1.20 | 1.11 | 2.01 |
| 32 | 5 | 1.61 | 1.41 | 1.44 |
| 33 | 4 | 1.24 | 1.99 | 2.08 |
| 34 | 4 | 1.33 | 2.12 | 2.51 |
| 35 | 4 | 1.19 | 2.47 | 2.64 |
| 36 | 5 | 1.99 | 3.66 | 4.54 |
| 37 | 4 | 1.21 | 1.67 | 1.23 |
| 38 | 3 | 0.99 | 1.45 | 1.65 |
| 39 | 5 | 1.88 | 2.49 | 2.48 |
| 40 | 4 | 1.07 | 2.04 | 2.98 |

TABLE 3

Statistical comparison between blood BHB content of the cattle treated with the bolus compositions of the present disclosure and those treated with bolus compositions having no rumen-protected choline

| | Cattle Treated with Bolus Compositions of the Present Disclosure | | | Cattle Treated with Bolus Compositions comprising no Rumen-protected Choline | | |
|---|---|---|---|---|---|---|
| | Day 0 | Day 3 | Day 6 | Day 0 | Day 3 | Day 6 |
| Average | 1.29 | 1.2615 | 1.246 | 1.269 | 1.857 | 2.2385 |
| SD | 0.366031 | 0.267528 | 0.294 | 0.290189 | 0.63619 | 0.88952 |
| Significant Difference? | No | Yes $P < 0.05$ | Yes $P < 0.05$ | No | Yes $P < 0.05$ | Yes $P < 0.05$ |
| Number with Subclinical Ketosis | 7 | 6 | 5 | 5 | 11 | 15 |

As shown in Table 3, there were cattle in both groups with subclinical ketosis after calving.

The average blood BHB concentration between the two groups of cattle was not statistically different at day 0. However, after treatment, the average blood BHB concentration of the cattle treated with the bolus compositions of the present disclosure lowered, while the average BHB concentration of the cattle treated with the bolus compositions of having no rumen-protected choline increased.

In fact, in the group treated with the bolus compositions of the present disclosure, the number of cattle with subclinical ketosis lowered from 7 to 5 over the course of the 6 days. In contrast, in the group treated with bolus compositions having no rumen-protected choline, the number of cattle with subclinical ketosis increased from 5 to 15 over the course of the 6 days.

Thus, the bolus compositions of the present disclosure are capable of reducing the incidence of subclinical ketosis in dairy cattle.

It will also be appreciated that, while the above study was conducted on dairy cattle, the findings are applicable to different types of ruminants including other types of cows such as beef cattle, sheep, goats, deer, and the like.

The invention claimed is:

1. A solid bolus composition for the simultaneous prevention or treatment of hypocalcemia and a choline deficiency in a ruminant, comprising:
   an inner mass comprising:
      a rumen-protected choline at about 5 wt % to about 20 wt % of the solid bolus composition;
      one or more calcium salts at about 65 wt % to about 85 wt % of the solid bolus composition;
      water at about 15 wt % to about 25 wt % of the solid bolus composition; and
      a binder at about 0.1 wt % to about 1 wt % of the solid bolus composition, and
   an outer mass being a coating comprising acetyl esters of triglycerides capable of passage through the esophagus for dissolution in the rumen of the ruminant to release the rumen-protected choline and the one or more calcium salts into the rumen,
      wherein the solid bolus composition has a total weight of between about 200 g and about 250 g and is for administration to the ruminant using a balling gun.

2. The solid bolus composition of claim 1, wherein the coating is present in an amount of about 5 g to about 10 g.

3. The solid bolus composition of claim 1, wherein the one or more calcium salts are one of calcium chloride, calcium sulphate, calcium carbonate, calcium propionate, calcium formate, calcium citrate, calcium iodate, calcium periodate, calcium lactate, calcium acetate, or any combination thereof.

4. The solid bolus composition of claim 1, wherein the one or more calcium salts comprise one or more calcium salt hydrates.

5. The solid bolus composition of claim 1, comprising two or more calcium salts having different release profiles.

6. The solid bolus composition of claim 1, comprising calcium chloride dihydrate and calcium sulphate hemihydrate.

7. The solid bolus composition of claim 6, wherein the calcium chloride dihydrate is present in an amount of about 45 wt % to about 55 wt % of the solid bolus composition.

8. The solid bolus composition of claim 6, wherein the calcium sulphate hemihydrate is present in an amount of about 20 wt % to about 30 wt % of the solid bolus composition.

9. The solid bolus composition of claim 1, further comprising a source of potassium, selenium, sodium, zinc, iodine, phosphorus, or any combination thereof.

10. The solid bolus of claim 1, further comprising vitamin A, vitamin D, vitamin E, or any combination thereof.

11. The solid bolus composition of claim 1, further comprising a wick.

12. The solid bolus composition of claim 11, wherein the wick is biodegradable in that the wick is degradable, dissolvable, or decomposable in the rumen of the ruminant.

13. The solid bolus composition of claim 11, wherein the wick is formed of cellulose or a cellulosic material.

14. The solid bolus composition of claim 1, wherein the shape of the bolus composition is spherical, cylindrical, capsular, torpedo-shaped or donut-shaped.

15. A method of preventing or treating hypocalcemia and/or a choline deficiency in a ruminant, the method comprising administering at least one of the solid bolus composition of claim 1 to the ruminant using a balling gun.

16. The solid bolus composition of claim 1, wherein the binder is xanthan gum.

* * * * *